(12) United States Patent
Chang

(10) Patent No.: US 9,539,265 B2
(45) Date of Patent: Jan. 10, 2017

(54) PHARMACEUTICAL FORMULATION CONTAINING GLYCOSAMINOGLYCAN

(71) Applicant: AIHOL CORPORATION, Las Vegas, NV (US)

(72) Inventor: Pao-Ho Chang, Hsinchu County (TW)

(73) Assignee: AIHOL CORPORATION, Las Vegas, NV (US)

( * ) Notice: Subject to any disclaimer, the term of this patent is extended or adjusted under 35 U.S.C. 154(b) by 0 days.

(21) Appl. No.: 14/771,207

(22) PCT Filed: Apr. 19, 2013

(86) PCT No.: PCT/US2013/037268
§ 371 (c)(1),
(2) Date: Aug. 28, 2015

(87) PCT Pub. No.: WO2014/143085
PCT Pub. Date: Sep. 18, 2014

(65) Prior Publication Data
US 2016/0008474 A1 Jan. 14, 2016

Related U.S. Application Data

(63) Continuation of application No. PCT/US2013/031817, filed on Mar. 15, 2013.

(51) Int. Cl.
| A61K 31/606 | (2006.01) |
| A61K 47/36 | (2006.01) |
| A61K 9/16 | (2006.01) |
| A61K 9/50 | (2006.01) |

(52) U.S. Cl.
CPC ........... *A61K 31/606* (2013.01); *A61K 9/5078* (2013.01); *A61K 9/5026* (2013.01); *A61K 9/5036* (2013.01)

(58) Field of Classification Search
CPC ..... A61K 9/1652; A61K 31/606; A61K 47/36
See application file for complete search history.

(56) References Cited

U.S. PATENT DOCUMENTS

| 4,980,173 A | 12/1990 | Halskov |
| 5,316,772 A | 5/1994 | Jurgens et al. |
| 5,541,170 A | 7/1996 | Rhodes et al. |
| 5,541,171 A | 7/1996 | Rhodes et al. |

(Continued)

FOREIGN PATENT DOCUMENTS

| JP | 63-101332 A | 5/1988 |
| JP | H04504404 A | 8/1992 |

(Continued)

OTHER PUBLICATIONS

Kathleen A Head et al., "Inflammatory bowel disease Part 1: ulcerative colitis-pathophysiology and conventional and alternative treatment options," Alternative Medicine Review, vol. 8, No. 3, pp. 247-283, 2003.

(Continued)

*Primary Examiner* — Michael B Pallay
(74) *Attorney, Agent, or Firm* — CKC & Partners Co., Ltd.

(57) ABSTRACT

A pharmaceutical formulation containing a glycosaminoglycan is provided. In this pharmaceutical formulation, a glycosaminoglycan layer surrounding a drug layer is used to improve the treatment efficiency of enteric diseases.

17 Claims, 5 Drawing Sheets

(56) References Cited

U.S. PATENT DOCUMENTS

| | | | |
|---|---|---|---|
| 6,046,179 A | 4/2000 | Murch et al. | |
| 6,551,620 B2 | 4/2003 | Otterbeck | |
| 6,773,720 B1 | 8/2004 | Villa et al. | |
| 6,893,662 B2 | 5/2005 | Dittmar et al. | |
| 2003/0161884 A1 | 8/2003 | Rosenberg et al. | |
| 2006/0246134 A1 | 11/2006 | Venkatesh | |
| 2009/0068263 A1 | 3/2009 | Antarkar et al. | |
| 2009/0181924 A1 | 7/2009 | Zoppetti et al. | |
| 2010/0285074 A1 | 11/2010 | Locke et al. | |
| 2010/0291201 A1 | 11/2010 | Shah et al. | |
| 2011/0189271 A1* | 8/2011 | Lad | A61K 9/00 424/451 |
| 2012/0058194 A1 | 3/2012 | Vaya et al. | |

FOREIGN PATENT DOCUMENTS

| | | |
|---|---|---|
| JP | 2002512195 A | 4/2002 |
| WO | 88/07365 A2 | 10/1988 |
| WO | 01/66094 A1 | 9/2001 |
| WO | 2012089768 A1 | 7/2012 |
| WO | 2012092486 A2 | 7/2012 |
| WO | 2012/136816 A2 | 10/2012 |
| WO | 2013006548 A2 | 1/2013 |

OTHER PUBLICATIONS

P. B. Patil et al., "Development and Evaluation of Mesalamine Tablet Formulation for Colon Delivery," Research J. Pharm. and Tech. 4(11):Nov. 2011; 1751-1756.

Xiao-yan Yang et al., "Hyaluronic acid-coated nanostructured lipid carriers for targeting paclitaxel to cancer," Cancer Letters, vol. 334, No. 2, pp. 338-345, Jul. 7, 2012.

S. Sudarshan et al., "Colon Specific Drug Delivery System of Mesalamine for Eradication of Ulcerative Colitis," Research Journal of Pharmacy and Technology, 2(4), pp. 819-823, Dec. 2009.

* cited by examiner

PHARMACEUTICAL FORMULATION CONTAINING GLYCOSAMINOGLYCAN

RELATED APPLICATIONS

This application is a continuation of International application No. PCT/US2013/037268, filed on Apr. 19, 2013, which claims priority of International application No. PCT/US2013/031817, filed on Mar. 15, 2013, the entirety of which is incorporated by reference herein.

BACKGROUND

Field of Invention

The disclosure relates to a pharmaceutical formulation. More particularly, the disclosure relates to a pharmaceutical formulation containing glycosaminoglycan.

Description of Related Art

Enteric coating has been developed for many years to improve the treatment efficiency of enteric diseases, and the used dose of drug can be thus decreased. However, the treatment efficiency of enteric diseases still needs improvement to further decrease the used dose of drug.

Mesalamine, also known as Mesalazine or 5-aminosalicylic acid (5-ASA), is an anti-inflammatory drug used to treat inflammation of the digestive tract ulcerative colitis and mild-to-moderate Crohn's disease. Mesalamine is a bowel-specific aminosalicylate drug that acts locally in the gut and has its predominant actions there, thereby having few systemic side effects. As a derivative of salicylic acid, mesalamine is also thought to be an antioxidant that traps free radicals, which are potentially damaging byproducts of metabolism. N-acetyl-5-ASA is a metabolite of 5-ASA. The absorbed 5-ASA is rapidly acetylated through the gut mucosal wall and by the liver. It is mainly excreted by the kidney, as N-acetyl-5-ASA.

U.S. Pat. No. 4,980,173 discloses a pharmaceutical composition containing as active ingredient 5-aminosalicylic acid or a pharmaceutically acceptable salt or ester thereof allow the treatment of colitis ulcerosa or Crohn's disease by oral administration. A particular slow-release tablet formation and its preparation were disclosed. The defect of the patent is that the drug distributes naturally in the intestine and dispersed not specific in interesting site, so it needs more dose to achieve better therapy result and will have less therapy effect owing to less dose of the drug adhered onto the inflammation part.

U.S. Pat. No. 5,541,170 discloses a solid dosage form, such as a capsule or tablet, containing a pharmacologically active agent is coated with an anionic polymer, which is insoluble in gastric juice and in intestinal juice below pH 7 but soluble in colonic intestinal juice, in a sufficient amount that the oral dosage form remains intact until it reaches the colon. Although this invention has specifically released the drug in the environment below pH 7, it still cannot aim the target to enhance the concentration of the drug on the disorder part. The defect is all the same as aforementioned.

U.S. Pat. No. 5,541,171 also discloses a solid dosage form that so much like U.S. Pat. No. 5,541,170. This patent just added more restriction terms comparing with the former one.

U.S. Pat. No. 6,551,620 discloses an orally administerable pharmaceutical pellet formulation for the treatment of the intestinal tract that is disclosed, which comprises a core and an enteric coating, the core including, as a pharmaceutical active compound, aminosalicylic acid or a pharmaceutically tolerable salt or a derivative thereof. The defect is still all the same as aforementioned.

U.S. Pat. No. 6,773,720 discloses a controlled-release oral pharmaceutical composition containing an active ingredient 5-amino-salicylic acid. The composition comprises: (a) an inner lipophilic matrix consisting of substances with a melting point below 90° C. in which the active ingredient is at least partly inglobated; (b) an outer hydrophilic matrix in which the lipophilic matrix is dispersed; and (c) optionally other excipients. The defect is still all the same as aforementioned.

U.S. Pat. No. 6,893,662 discloses a pharmaceutical composition in a solid unit dosage form for oral administration in a human or lower animal. The pharmaceutical composition comprises: (a) a safe and effective amount of a therapeutically active agent; (b) an inner coating layer selected from the group consisting of poly(methacrylic acid, methyl methacrylate) 1:2, poly(methacrylic acid, methyl methacrylate) 1:1, and mixtures thereof; and (c) an outer coating layer comprising an enteric polymer or film coating material. However, the defect is still all the same as aforementioned.

U.S. Pat. No. 6,046,179 discloses a composition for treating inflammatory bowel disease in a patient suffering from inflammatory bowel disease comprising: (a) a therapeutic amount of N-acetyl-glucosamine; and (b) a pharmacologically acceptable carrier, adapted to be administered colonically to said patient. The defect of this patent is that it was short of a drug other than N-acetyl-glucosamine; therefore, it lacks supplement each other between N-acetyl-glucosamine and the other drug, such as mesalamine.

Since the compositions of these patents above all have to be used under regular doses of either drug or N-acetyl-glucosamine, these compositions cannot decrease the general therapeutic dose (amount) of either one.

Glycosaminoglycan can be obtained from numerous sources (e.g. rooster combs, trachea, umbilical cords, skin, articular fluids and certain bacteria such as *Streptococci* spp). Most glycosaminoglycans are composed of repeating sugars such as N-acetyl glucosamine, N-acetyl glucuronic acid and/or N-acetyl galactosamine (these are known as non-sulfated glycosaminoglycans). If such glycosaminoglycans contain sulfur groups they are known as sulfated glycosaminoglycans. Examples of glycosaminoglycans include hyaluronic acid (which is made up of repeating units of N-acetyl glucosamine and glucuronic acid), chondroitin sulphate, dermatan sulphate, keratan sulphate and heparin, all of which contain either N-acetylglucosamine or the amino sugar, N-acetylgalactosamine. Glycosaminoglycans are also presented in proteoglycans, which are structures containing a number of glycosaminoglycans chains linked to a polypeptide or a protein core.

SUMMARY

Accordingly, in one aspect, the present invention is directed to a pharmaceutical formulation containing at least a pellet to improve the treatment efficiency of enteric diseases.

According to another embodiment, the pellet above comprises a core, a drug layer surrounding the core, a glycosaminoglycan layer surrounding the drug layer, an isolation layer surrounding the glycosaminoglycan layer, and an enteric coating layer surrounding the isolation layer.

Accordingly, the weight ratio of the core, the drug layer, the glycosaminoglycan layer, the isolation layer, and the enteric coating is 100:137-141:25-29:9-13:60-64, and preferably 100:139:27:11:62.

According to an embodiment, the pellet above comprises a core, a drug layer surrounding the core, a glycosaminoglycan layer surrounding the drug layer, and an enteric coating layer surrounding the glycosaminoglycan layer.

Accordingly, the weight ratio of the core, the drug layer, the glycosaminoglycan layer, and the enteric coating is 100:137-141:25-29:60-64, and preferably 100:139:27:62.

In one embodiment the core above comprises a pharmaceutical acceptable inert material, such as cellulose, starch, sugar, or silicon oxide; preferably, microcrystalline cellulose.

In another embodiment, the drug layer above comprises a drug for treating an enteric disease.

In another embodiment, the drug layer above comprises a drug including mesalamine, laxatives, anti-diarrheals, glucocorticoids, antimicrobials, immunosuppressants, chemotherapeutics, anti-cancer drugs, peptides, proteins, cardiovascular drugs, psychotropic drugs, H2-blockers, antiasthmatic agents, antihistamines, steroid, non-steroid anti-inflammatory drug (NSAID), antibiotic, anti-inflammatory, or any derivatives thereof.

In yet another embodiment, the drug layer above further comprises a binder like hydroxypropylmethyl cellulose, hydroxypropyl cellulose, or polyvinylpyrrolidone.

In yet another embodiment, the glycosaminoglycan layer comprises hyaluronic acid or a salt thereof, chondroitin sulfates, heparin sulfate, heparin, keratan sulfate, or dermatan sulfate, for example.

In yet another embodiment, the isolation layer comprises a hydrophobic polymer, which can be dissolved at a pH value of at least 5.5. The hydrophobic polymer can be poly(methacrylic acid-co-ethyl acrylate) 1:1, poly(methacylic acid-co-methyl methacrylate) 1:1, poly(methyl acrylate-co-methyl methacrylate-co-methacrylic acid) 7:3:1, cellulose acetate phthalate, cellulose acetate succinate, methylcellulose phthalate, methylhydroxypropyl-cellulose phthalate, ethylhydroxyceilulose phthalate, polyvinylacetate phthalate, polyvinylbutyrate acetate, vinyl acetate-maleic anhydride copolymer, styrene-maleic mono-ester copolymer, methyl acrylate-methacrylic acid copolymer, and methacrylate-methacrylic acid-octyl acrylate copolymer, for example.

In yet another embodiment, the isolation layer or the enteric coating layer comprises an enteric polymer(s) or pH resistant polymer(s), which can be dissolved at a pH value of at least 6.8. The enteric polymer(s) can be cellulose acetate phthalate, cellulose acetate succinate, methylcellulose phthalate, ethylhydroxycellulose phthalate, polyvinylacetate phthalate, polyvinylbutyrate acetate, vinyl acetate-maleic anhydride copolymer, styrene-maleic mono-ester copolymer, methyl acrylate-methacrylic acid copolymer, methacrylate-methacrylic acid-octyl acrylate copolymer, or any combinations thereof, for example.

In yet another embodiment, the pellet is in a capsule or a tablet.

The foregoing presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later. Many of the attendant features will be more readily appreciated as the same becomes better understood by reference to the following detailed description considered in connection with the accompanying drawings.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1A:
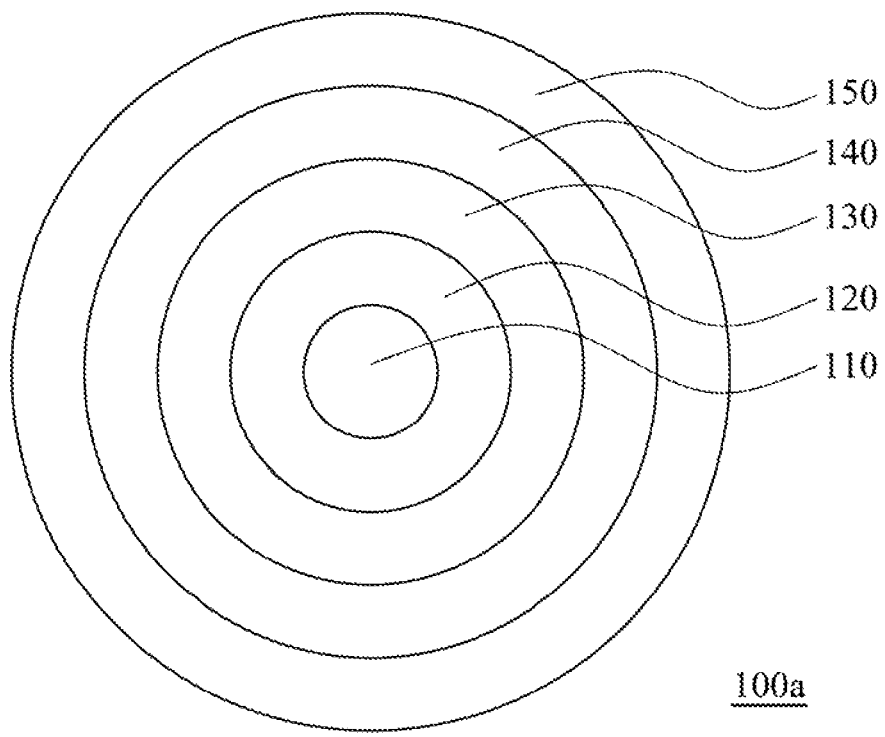
FIG. 1A is a diagram of a pellet's structure according to an embodiment of this invention.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Definitions of Terms

"Subject" as used herein is any mammal. Subjects include individuals in need of drug (e.g. mesalamine) treatment (patients) and individual's not in need of drug treatment (e.g. normal healthy volunteers). Humans are preferred subjects and patients.

A "therapeutically effective amount" or "effective amount" of a drug (e.g. mesalamine) is an amount needed to achieve a desired pharmacologic effect or therapeutic improvement without undue adverse side effects. The effective amount of a drug (e.g. mesalamine) will be selected by those skilled in the art depending on the particular patient and the disease. It is understood that "an effect amount" or "a therapeutically effective amount" can vary from subject to subject, due to variation in metabolism of a drug (e.g. mesalamine), age, weight, general condition of the subject, the condition being treated, the severity of the condition being treated, and the judgment of the prescribing physician. Furthermore, persons of ordinary skill in the art can clearly understand the "amount" or "dose" according to the packing insert or label of the drug registered in the drug administration competent authority ratified by responsible institution of medicine management.

"Treat" or "treatment" refers to any treatment of a disorder or disease, such as preventing the disorder or disease from occurring in a subject which may be predisposed to the disorder or disease, but has not yet been diagnosed as having the disorder or disease; inhibiting the disorder or disease, e.g., arresting the development of the disorder or disease, relieving the disorder or disease, causing regression of the disorder or disease, relieving a condition caused by the disease or disorder, or reducing the symptoms of the disease or disorder.

Introduction

The present invention is based on the previous test results of the inventors, wherein the amount of hyaluronic acid (HA) binding onto the inflammatory surface was higher than the non-inflammatory area of colon tissue. Further, the results indicated that HA can be taken as a delivery vehicle to carry a drug, such as mesalamine, suitable for the treatment of an inflammation and/or allergy and/or injury when HA was mixed with a drug. Therefore, the concentration of the drug is higher in inflammatory surface than in non-inflammatory area when combining use of HA and mesalamine. Accordingly, the dose of the drug can be decreased than regular dose, and the therapy effect is also highly improved owing to the drug especially adhering onto the place that needs cure. Accordingly, the present invention is in the light of aforesaid results to further develop the formulation of the present invention.

Pharmaceutical Formulation Containing a Pellet

Accordingly, an aspect of this invention is to provide a pharmaceutical formulation containing at least a pellet to improve the treatment efficiency of enteric diseases. The pellet is a controlled release formulation (also known as a delay release formulation), which is designed to deliver a drug over an extended period of time, that is, to release a drug at any time other than immediately after administration and/or at any other location in the gastrointestinal tract more distal to that which would have been accomplished by an immediate release dosage form.

Figure 1B:
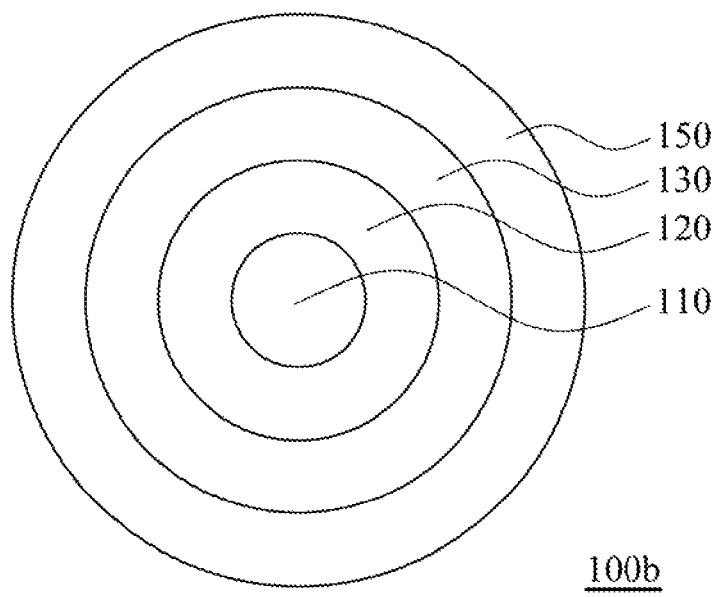
FIG. 1B is a diagram of a pellet's structure according to another embodiment of this invention.

The structure of the each pellet in this pharmaceutical formulation is shown in FIG. 1A or 1B. The pharmaceutical formulation comprises capsule, tablet, or any other kinds of formulation that need at least a pellet. That is, the pellets can be encapsulated in a capsule or be compressed into a tablet.

FIG. 1A is a diagram of a pellet's structure according to an embodiment of this invention. In FIG. 1A, a pellet 100a sequentially includes a core 110, a drug layer 120, a glycosaminoglycan layer 130, an isolation layer 140, and an enteric coating layer 150, from the inside out. The weight ratio of the core 110, the drug layer 120, the glycosaminoglycan layer 130, the isolation layer 140, and the enteric coating layer 150 are shown as Table 1.

TABLE 1

Weight ratio of each part in the pellet 100a

| Component | Weight Ratio |
|---|---|
| Core 110 | 100 |
| Drug layer 120 | 137-141 |
| Glycosaminoglycan layer 130 | 25-29 |
| Isolation layer 140 | 9-13 |
| Enteric coating layer 150 | 60-64 |

The core 110 is used as a coating seed to facilitate the coating of the subsequently layers. Therefore, the diameter of the core 110 is about 500-800 μm, such as 700 μm. The composition of the core 110 can be any pharmaceutically acceptable inert material, such as cellulose, starch, sugar, or silicon dioxide. The cellulose can be methyl cellulose, hydroxypropylmethyl-cellulose, sodium carbomethylcellulose, or microcrystalline cellulose, for example. The starch can be or from maize starch, wheat starch, rice starch, potato starch, or corn starch, for example. The sugar can be maltose, lactose, fructose, galactose, trehalose, sucrose, mannitol, or sorbitol, for example.

The drug layer 120 contains a drug that is suitably for treating an enteric disease. For example, for treating enteritis, the drug can be antibiotic or antispasmodic. For treating peptic ulcer, the drug can be coagulant, antibiotics, antacid, H2 blocker, potassium hydrogen ion pump blocker (PPI), cytoprotectives, or mucosa protector. For treating inflammatory bowel disease (IBD), the drug can be steroid, immunosuppressive agent, antibiotic, 5-ASA (5-aminosalicylic acid) and derivatives, or anti-inflammatory. Accordingly, the drug can be any of aforementioned, for example. Preferably, the drug in the drug layer 120 contains a positively charged functional group.

The drug layer 120 can further comprise a binder for binding the power of the drug to the core 110. The binder can be hydroxypropylmethyl cellulose, hydroxypropyl cellulose, or polyvinylpyrrolidone, for example.

The glycosaminoglycan layer 130 majorly contains a glycosaminoglycan, which is used to bridge the drug in the drug layer 120 and enteric mucosa in gastrointestinal tract. The glycosaminoglycan can be hyaluronic acid, chondroitin sulfates, heparin sulfate, heparin, keratan sulfate, or dermatan sulfate.

According to an embodiment, the glycosaminoglycan is hyaluronic acid. Hyaluronic acid (abbreviated as HA below) is an anionic, nonsulfated glycosaminoglycan distributed widely throughout connective, epithelial, and neural tissues. Therefore, HA has high affinity with biological tissues, such as mucosa. Since HA contains a negatively charged carboxylate group, HA can interact with a positively charged functional group. Therefore, if the drug in the drug layer 120 has a positively charged functional group, HA can interact with the drug to fix the drug onto the enteric mucosa to concentrate drug in a specific area like injure part therefore, enhance the effect and efficiency of the drug for better treatment of the enteric disease and for less waste of the drug administered. This phenomenon can also be construed by pilot result of the present invention, which showed more tightly adhesion on injured area than normal area.

The isolation layer 140 is used to protect the glycosaminoglycan layer 130 from contacting water during the pellet's later preparation steps. When the glycosaminoglycan in the glycosaminoglycan layer 130 is HA, since HA will easily form a HA film after contacting water, a problem of aggregating the pellets is produced to obstruct coating. Therefore, the material used for the isolation layer 140 can be a hydrophobic polymer, which can be dissolved at a pH value of at least 5.5.

The hydrophobic polymer can be poly(methacrylic acid-co-ethyl acrylate) 1:1, poly(methacylic acid-co-methyl methacrylate) 1:1, poly(methyl acrylate-co-methyl methacrylate-co-methacrylic acid) 7:3:1, cellulose acetate phthalate, cellulose acetate succinate, methylcellulose phthalate, methylhydroxypropyl-cellulose phthalate, ethylhydroxycellulose phthalate, polyvinylacetate phthalate, polyvinylbutyrate acetate, vinyl acetate-maleic anhydride copolymer, styrene-maleic mono-ester copolymer, methyl acrylate-methacrylic acid copolymer, or methacrylate-methacrylic acid-octyl acrylate copolymer. These hydrophobic polymers may be used either alone or in combination, or together with other polymers than those mentioned above.

The enteric coating 150 majorly contains an enteric polymer, which is preferentially soluble in the less acid environment of the small intestine, large intestine, or both relative to the more acid environment of the stomach. It is expected that any anionic polymer exhibiting a pH-dependent solubility profile can be used as an enteric coating in the practice of the present invention. According to an embodiment, the enteric polymer can be dissolved at a pH value of at least 6.8. The enteric polymer can be cellulose acetate phthalate, cellulose acetate succinate, methylcellulose phthalate, ethylhydroxycellulose phthalate, polyvinylacetate phthalate, polyvinylbutyrate acetate, vinyl acetate-maleic anhydride copolymer, styrene-maleic mono-ester copolymer, methyl acrylate-methacrylic acid copolymer, methacrylate-methacrylic acid-octyl acrylate copolymer, etc. These enteric polymers may be used either alone or in combination, or together with other polymers than those mentioned above.

FIG. 1B is a diagram of a pellet's structure according to another embodiment of this invention. In FIG. 1B, the isolation layer 140 of the pellet 100a in FIG. 1A is omitted to form the structure of the pellet 100b.

Method of Preparing Pellets in the Pharmaceutical Formulation

Another aspect of this invention is to provide a method of preparing pellets filled in capsules or tablets. Each layer of the pellet 100a or 100b shown in FIG. 1A or 1B is coated by a fluid bed system (purchased from Huttlin, German). The coating solutions for the each layer of the pellet 100a or 100b are described below.

For the coating of the drug layer 120, the drug coating solution is prepared by the following steps. First, at least one of the binders above is added to water and stirred to form a clear solution having a viscosity of 4.8 to 7.2 cP (centipoise). Then, the binder's clear solution was sequentially added by an anti-caking agent and a drug, and then stirred to form a uniform drug coating solution. The anti-caking agent, such as talc (i.e. hydrated magnesium silicate), is used to avoid the aggregation of pellet.

For the coating of the glycosaminoglycan layer 130, the glycosaminoglycan coating solution is prepared by the following steps. A binder is first added to ethanol (99.9%) and stirred to form a clear solution. A glycosaminoglycan is than added to the binder's clear solution, and then stirred to form a uniform glycosaminoglycan coating suspension. The binder can be hydroxypropyl cellulose (such as HPC-L).

For the coating of the isolation layer 140, the isolation coating solution is prepared by the following steps. A hydrophobic polymer is added to ethanol (95%) and stirred to form a clear solution. Then, triethyl citrate and talc are added to the clear solution of the hydrophobic polymer and stirred to form a uniform isolation coating solution.

For the coating of the enteric coating layer 150, the enteric coating solution is prepared by the following steps. At least an enteric polymer, an emulsion containing water, glyceryl monostearate, triethyl citrate and polysorbate 80 (PlasACRYL-T20), and water are mixed to form a uniform solution. The solution is then filtered by a 60 mesh sieve.

Embodiment 1

The Adhesion of HA in Colon Tissue

Procedure:

(I) 0.25 g of high molecular weight sodium hyaluronate powder (abbreviated as HHA; MW: 2 MDa; Freda) and 0.25 g of low molecular weight sodium hyaluronate powder (abbreviated as LHA; MW: 350 kDa; Freda) were added into 50 ml PBS buffer (Phosphate buffered saline) respectively to form a 0.5% solution, and then stirred for 6 hours until the powder was totally dissolved. 0.05 g LHA powder and 0.2 g HHA powder (ratio 2:8, and average MW is 1 MDa; denoted as medium molecular weight sodium hyaluronate powder, and abbreviated as MHA) were added into 50 ml PBS buffer, and then stirred for 6 hours until the powder was totally dissolved.

(II) Fluorescent HA (abbreviated as HA-f) was prepared by the following steps:

(1) MES buffer solution: 0.39 g MES free acid (2-(N-morpholino)ethanesulfonic acid, Calbiochem) and was dissolved in 100 ml dd (double distilled) water.

(2) Solution A: 65 mg fluroresceinamine powder, (isomer I, Fluka) was dissolved in 9 ml 95% EtOH solution and then stirred for 10 minutes under a condition that light was prohibited.

(3) Solution B: 359 mg EDC powder [N-(3-Dimethylamino propyl)-N-ethyl carbodiimide hydrochloride, Sigma] was dissolved in 9 ml MES buffer and then stirred for 10 minutes.

(4) Solution C: 216 mg NHS powder (N-Hydroxysuccinimde, Sigma) was dissolved in 9 ml MES buffer and then stirred for 10 minutes.

(5) 3 ml Solution A was slowly dropped into 50 ml of 0.5% HA solution and then stirred for 10 minutes under a condition that light was prohibited.

(6) 3 ml Solution B and 5 ml Solution C were separately dropped into the solution of step (5), and then stirred for 10 minutes under a condition that light was prohibited.

(7) 0.02 M MES buffer solution was slowly added into the solution of step (6) until the volume reached 100 ml, and then stirred for 24 hours at room temperature under a condition that light was prohibited.

(8) The product after reaction was poured into a dialysis tubing (MW: 12000~14000) in 5 L dd water as a dialysis solution and then stirred for 5 days at 4° C. under a condition that light was prohibited with dialysis solution being changed every 12 hours until the dialysis solution had no fluorescence.

(9) The liquid after dialysis was allocated into 50 mL plastic centrifuge tubes and then reserved at −20° C. refrigerator overnight followed by drying in a freeze-drying machine under a condition that light was prohibited.

(10) The dried HA-f powder was reserved at −20° C. refrigerator.

(11) 50 mg HA-f powder was slowly added into 10 ml PBS buffer and then stirred for 6 hours until the powder was totally dissolved.

(III) Colon tissue of SD-rat (Sprague-Dawley Rat) aged 7-8 weeks was cut by scalpel and then washed by PBS buffer followed by being cut to 3-4 cm long with soaking in PBS buffer finally.

(IV) Injured colon tissue was prepared by brushing by toothbrush for 20 times longitudinally and then soaking in PBS buffer.

(V) Normal and injured colon tissues were put into 12-well plates and then 1 ml 0.5% HA-f solution was added into each well and shaken for 2 hours at room temperature. Surplus HA-f solution was sucked by tip 2 hours later, and then soaked into PBS buffer for 10 minutes followed by removing PBS buffer repeatedly for 3 times.

(VI) Cleaned colon tissue was placed in a 12-well plate with lining tissue upwards and then placed onto the dock of the IVIS (in vivo image system, XENOGEN). The default parameter was set up as GFP (green fluorescent protein) whereas the excitation was 465 nm and the emission was 500 nm and then the image was captured by software.

(VII) All values in the table are expressed as means of n observations. The histological index was analyzed by Student's t-test.

Figure 2:
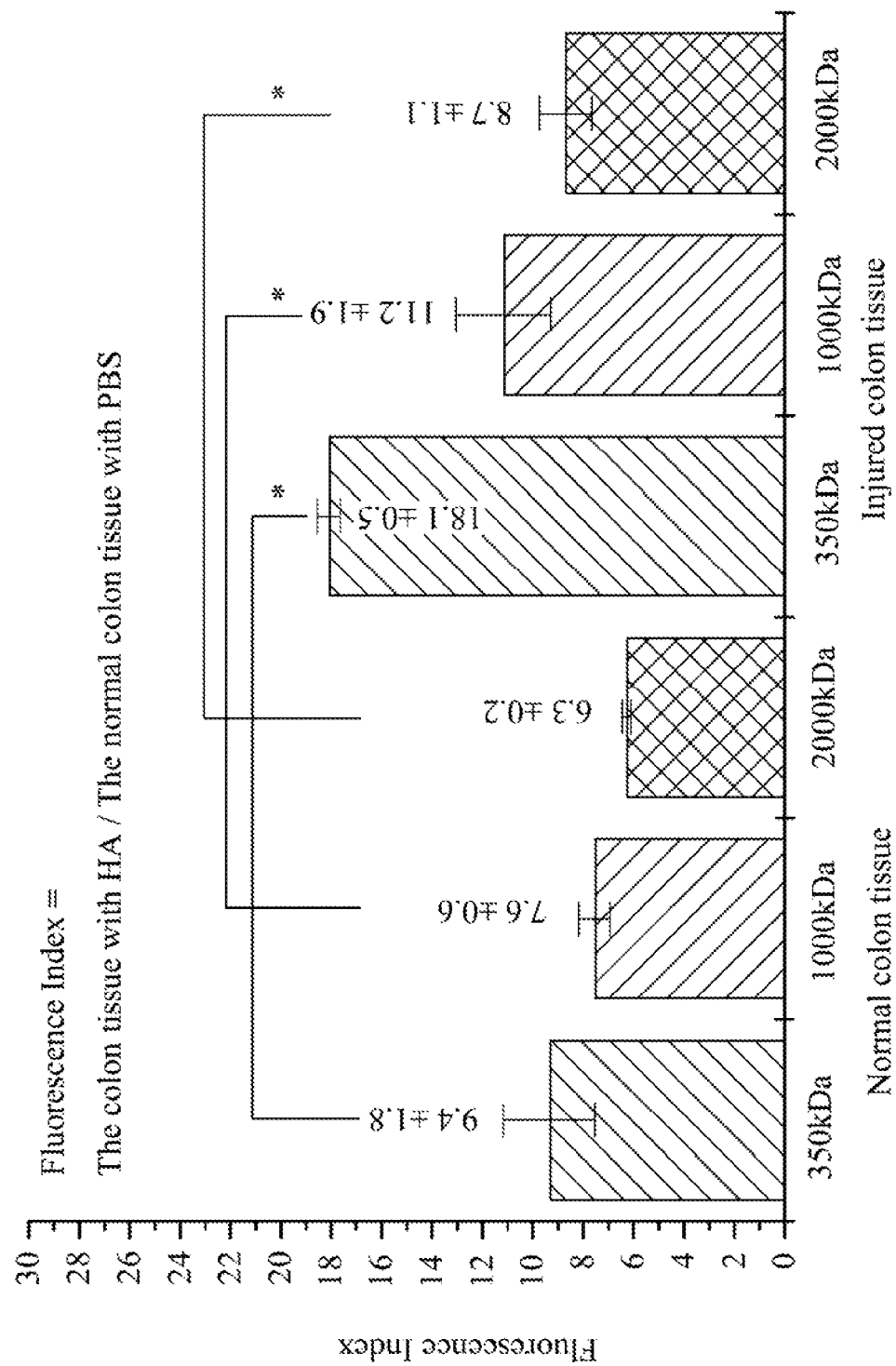
FIG. 2 shows the affinity of HAs by fluorescent index in normal and injured colon tissues ($*p<0.05$).

Result:

FIG. 2 shows the affinity of HAs by fluorescent index in normal, and injured colon tissues (*p<0.05). In FIG. 2, the fluorescent index of normal colon tissue was defined as 1. The other colon tissues tests were calibrated by the fluorescent index of normal colon tissue. The result showed that the adhered amount of the HAs with the same average MW were obviously higher in the injured colon tissues than in the normal colon tissues (P<0.01). Comparing the different adhered amount of the HAs with three different average molecular weights (i.e. HHA, MHA, and LHA) in the injured colon tissues, the fluorescent index of the adhesion of 350 KDa HA (i.e. LHA) by the injured colon tissues was obviously higher than those of the other two HAs with MW of 2 MDa and 1 MDa (i.e. HHA and MHA).

Embodiment 2

Comparative Study of Colon Tissue Concentration of Mesalamine after Intraluminal Instillation of Different Mesalamine Preparations Procedure:
(I) Experimental Animals:
8-week-old male SPF-grade Sprague-Dawley rats (280~330 g) were supplied by BioLASCO Taiwan Co. Ltd.
(II) Test Drugs:
(A) Colasa® enema (20 mg/ml, United Biomedical, Inc. Asia), and
(B) 0.25% (w/w) HA mixture (8:2=2000 KDa HA: 350 KDa HA) in PBS (pH7.4) containing 5 mg/mL mesalamine (abbreviated as HA-M).
(III) Intraluminal Instillation of Test Drugs:
After lightly anesthetized by Zoletil 50, rat ventral incision was made by surgical scissors, and colon was identified. 2 segments of colon (2 cm each) were tied by cotton threads, 0.5 ml of test drugs were injected into the lumen of isolated colon segments. After 0.5, 1, 1.5, or 2 hours, rats were sacrificed, and colon segments were removed. For each time point of intraluminal instillation, three rats were used.
(IV) Preparation of Specimens:
Tissue biopsies were washed with PBS solution to remove the surface contamination, weighed and immediately frozen in liquid nitrogen, and stored at −80° C. until use. Biopsies were crushed and 50 mM $KH_2PO_4$ solution (pH 7.4) was added. Tissue cells were disrupted ultrasonically using a microprobe inserted into the suspension for 10 seconds, and then ultrasonic disruption was stopped for 20 seconds at 25 W for a total of 10 minutes. After mixing by Vortex, samples stood for 30 minutes at room temperature, to permit protein precipitation, and were then centrifuged at 13000 g for 30 minutes.
(V) Analysis of Mesalamine Concentration in Colon Tissue Biopsies:
Mesalamine was measured by ultra performance liquid chromatography (UPLC). The method has been validated. Waters (UK) ACQUITY system and fluorescence detector (excitation 315 nm, emission 430 nm) were employed, and the data were analyzed using Empower 2. An ACQUITY column (C18, 100×2.1 mm internal diameter, 1.7 um particle) purchased from Waters (UK) was protected by a Van guard column (C18, 5×2.1 mm internal diameter, 1.7 um particles, Waters). The mobile phase consisted of 0.1 M acetic acid with triethylamine at pH 4.3 and acetonitrile (850:150). The flow-rate was 0.2 mL/min, with a resulting pressure of 5400 psi, and the analysis was performed at 40° C. Injection volume was 5 µl. Samples were derivatized using propionic anhydride to enhance the fluorescence characteristics of mesalamine. Triethylamine was used as an ion-pairing agent to improve peak symmetry. The UPLC method of mesalamine analysis was validated for measuring mesalamine over a nominal linear range of 10 to 1000 ng/ml. The linear correlation coefficient ($R2$) of the method used in this study is 1.00.

Figure 3:
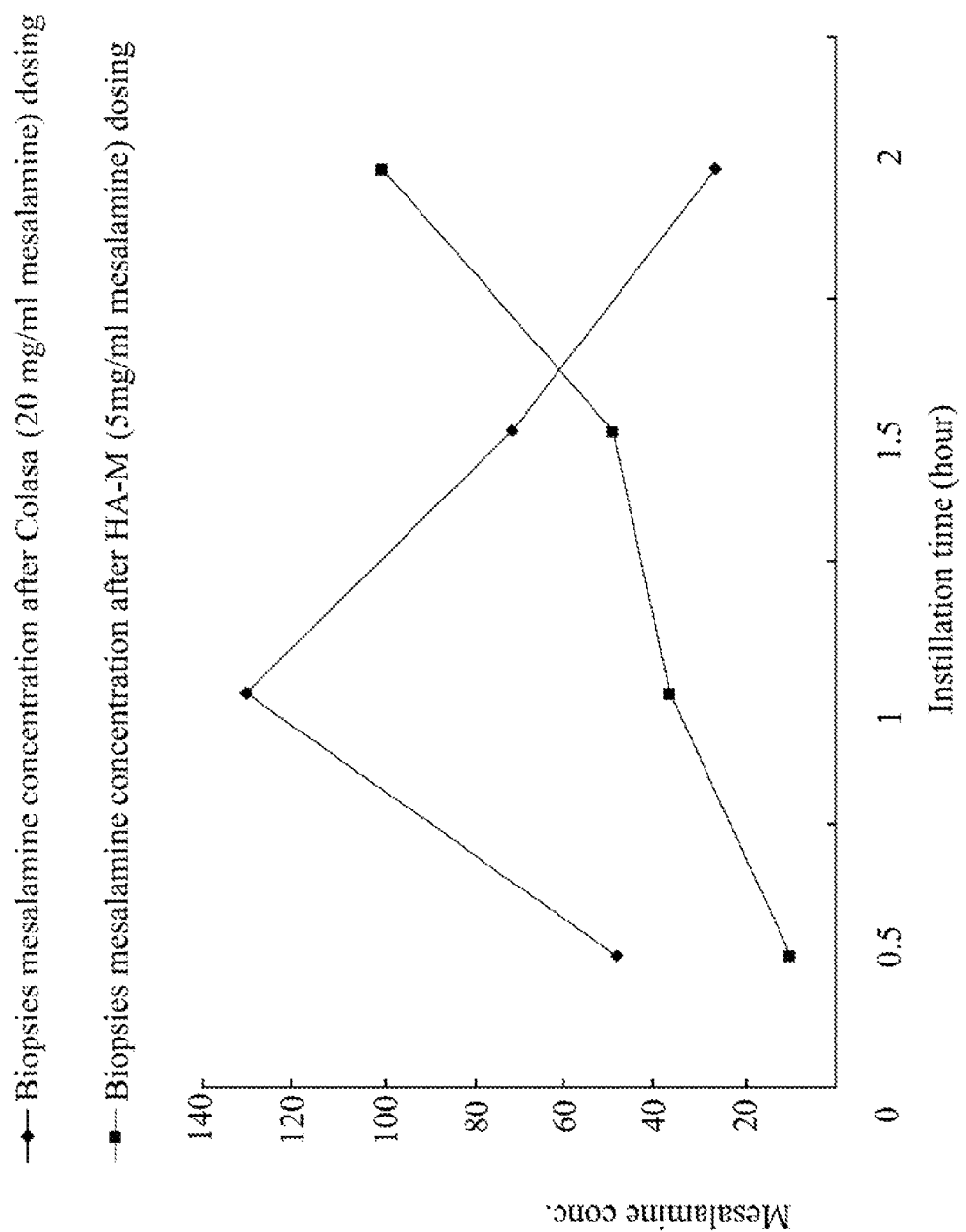
FIG. 3 shows colon tissue biopsies time, mesalamine concentration profile after Colasa® (a brand of enema preparation with 20 mg of mesalamine in 1 ml solution) or HA-mesalamine dosing.

Results:
FIG. 3 shows colon tissue biopsies time, mesalamine concentration profile after Colasa® (a brand of enema preparation with 20 mg of mesalamine in 1 ml solution) or HA-mesalamine (abbreviated as HA-M) dosing. In FIG. 3, the (median) concentration of mesalamine in colon tissue biopsies after instillation of Colasa® peaked after one hour instillation. After that, the concentration of mesalamine dropped rapidly. On the contrary, HA-M continuously released mesalamine during the two-hour period and the concentration of mesalamine was rising and much higher than that of Colasa® after two-hour instillation.

The result of this embodiment disclosed that HA-M sustained the release of mesalamine much longer as compared to the commercial mesalamine enema (Colasa®). However, HA-M contained only one-fourth the concentration of mesalamine in Colasa®. The result of the data above showed that only one-fourth of the regular therapeutically effective amount was used in the HA-M, but HA-M has almost the same efficacy to ameliorate the inflammation of artificially induced IBD in rats.

Embodiment 3

Dissolution Test of the Pellets

In this embodiment, pellets were produced according to the preparation method provided above. The materials used for each layer are listed in Table 2 below.

TABLE 2

| Layer | Ingredient (trade name) | Weight (mg) | *Diameter or *thickness (µm) |
|---|---|---|---|
| Core | microcrystalline cellulose (Cellets 500) | 160.0 | 652 |
| Drug layer | talc | 8.0 | 900 |
| | hydroxypropylmethyl cellulose (HPMC 606) | 15.0 | |
| | Mesalamine (drug) | 200.0 | |
| glycosaminoglycan layer | Sodium Hyaluronate | 31.25 | 911 |
| | Hydroxypropyl Cellulose (Grade L) | 11.75 | |
| Isolation layer | poly(methacylic acid-co-methyl methacrylate) 1:1 (Eudragit L100) | 11.0 | 935 |
| | Talc | 6.0 | |
| | triethyl citrate | 1.0 | |
| Enteric coating layer | poly(methyl acrylate-co-methyl methacrylate-co-methacrylic acid) 7:3:1 (Eudragit FS30D) | 81.0 | 943 |
| | poly(methacrylic acid-co-ethyl acrylate) 1:1 (Eudragit L30D-55) | 9.0 | |
| | emulsion containing water, glyceryl monostearate, triety citrate and polysorbate 80 (PlasACRYL-T20) | 9.0 | |

*Measured by scanning electron microscope (SEM).

Then, a dissolution experiment was performed for the pellets above. In this dissolution experiment, 6 capsules were used for each dissolution test. The pH values of the buffer solutions used to dissolute the capsules were 4.5 and 6.8, respectively. The pH 4.5 buffer solution was prepared by mixing solutions of $KH_2PO_4$ and $H_3PO_4$, and the pH 6.8 buffer solution was prepared by mixing solutions of $KH_2PO_4$, NaOH and KOH. The dissolution tests were performed at 37.0±0.5° C., and the paddle was rotated at 100 rpm. The online UV detector was set at 330 nm for detecting the concentration of the dissolved mesalamine. Various amounts of mesalamine were dissolved in a certain amount of pH 4.5 or pH 6.8 buffer solutions to be the standard samples for determining the concentration of the dissolved mesalamine.

Figure 4A:
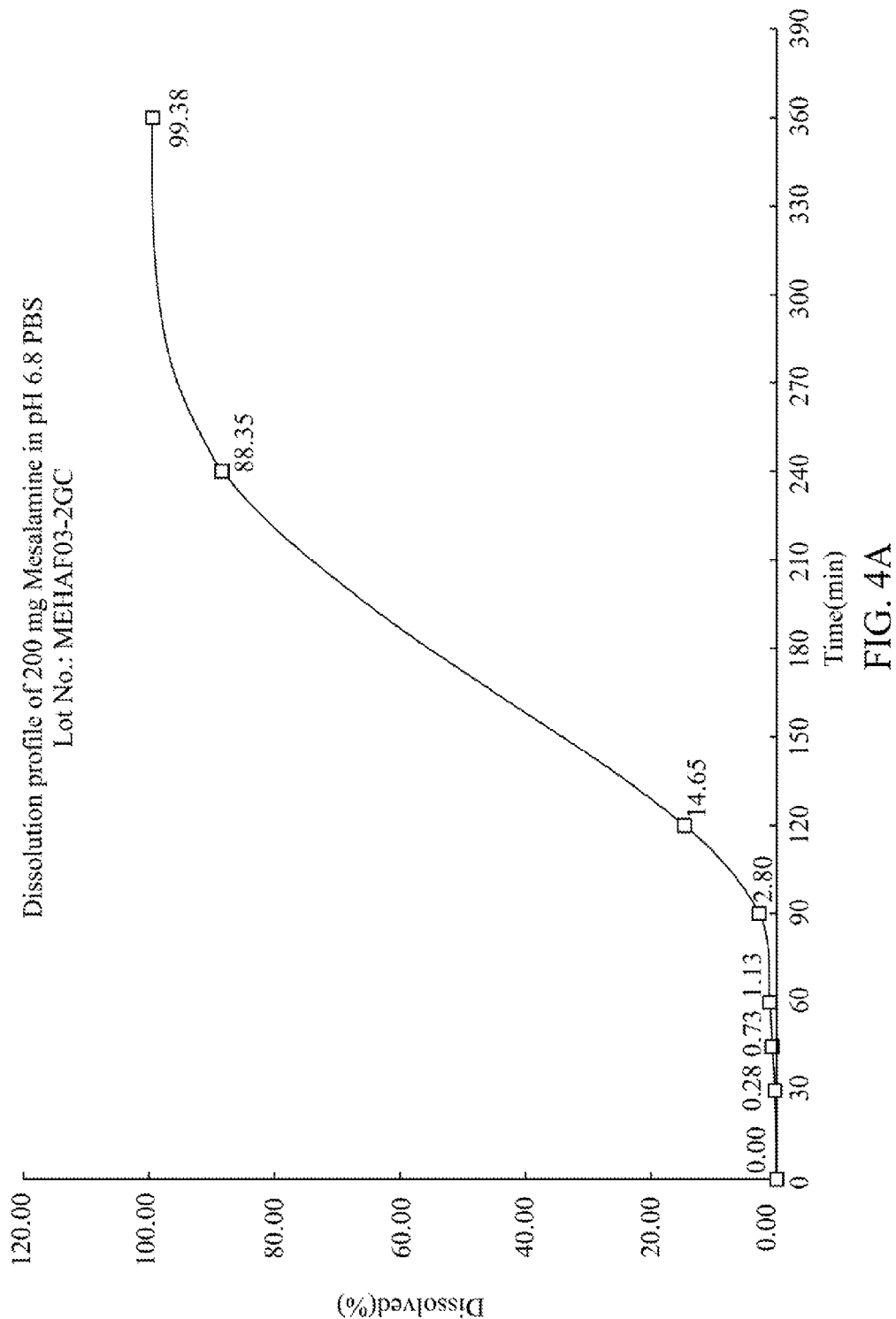
FIGS. 4A and 4B are the dissolution profiles of the pellets dissolved in pH 6.8 and pH 4.5 buffer solutions.
Figure 4B:
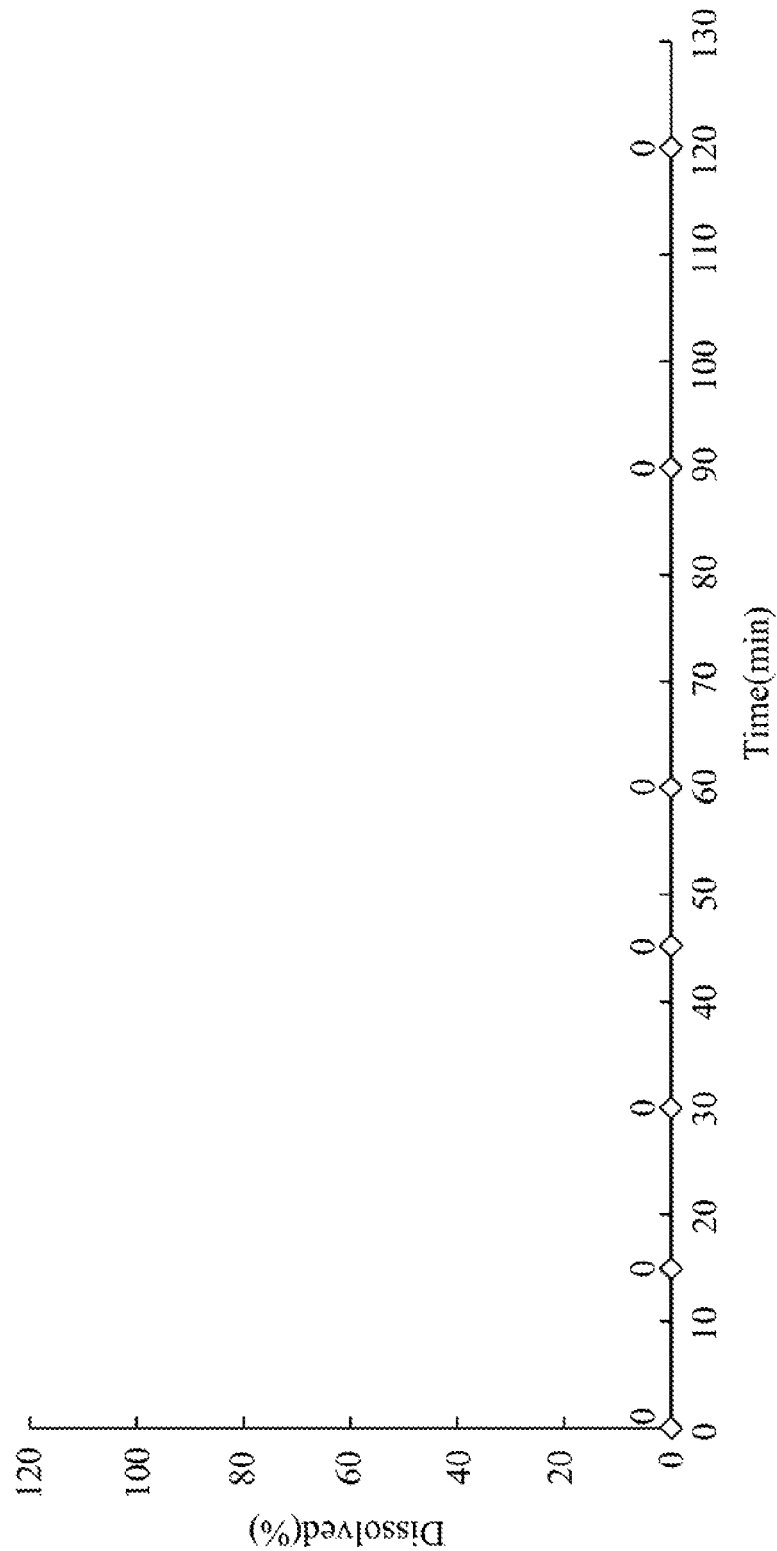

FIGS. 4A and 4B are the dissolution profiles of the pellets dissolved in pH 6.8 and pH 4.5 buffer solutions. In FIG. 4A, the dissolution rate of the pellets rapidly increased from 90 minutes. However, in FIG. 4B, the pellets did not dissolve in pH 4.5 buffer solution for at least 2 hours. Accordingly, it can be known that the pellets of this embodiment can dissolve in pH 6.8 buffer solution, i.e. the enteric environment, but cannot dissolve in pH 4.5 buffer solution, i.e. the gastric environment.

Embodiment 4

Healing Efficacy of Pellets 100a on DNBS-Induced Pig Model for Colitis

Procedure:

(I) Swine was selected form LY strain hog (father's side was Landrace; mother's side was Yorkshire). The age during the test was 9 weeks±1 week. 9 swines were divided into three groups: A, B and C.

(II) Reagents:
 (a) 40 mg/ml of Stresnil (from China Chemical & Pharmaceutical Co., Ltd., Taiwan) for sedation of swine.
 (b) 50 mg/ml of Zoletil-50 (from Virbac Laboratories, France) for anesthesia of swine.
 (c) 1 mg/ml of Atropine (from Tai Chemical & Pharmaceutical Co., Ltd, Taiwan) for inhibition of saliva secretion while combining with Zoletil-50.
 (d) 150 mg/ml of 2,4-dinitrobenzene sulfonic acid (DNBS) dissolved in 50% ethanol (from Sigma-Aldrich Co. USA).

(III) Test drug:
Group A: The enteric coated pellets 100a within a capsule with the active dose of 200 mg 5-ASA/capsule.
Group B: Starch with a capsule as control.
Group C: Reference drug, trade name Pentasa, with 500 mg 5-ASA/capsule.

(IV) All swines were fasted for 2 days. On day 1, the swines were anesthetized for inspecting the situation of large intestine by gastric intestinal endoscope.

(V) 40 ml of DNBS (150 mg/mL) was administrated via the rectum and retained in the colon for 1 hour to induce colitis; after which the residual DNBS was withdrawn, then washed the rectum by 100 ml distilled water.

(VI) On days 7, 14, 35 and 49, the induced situations of intestine at the sites of 40, 35, 30, 25, 20, 15, 10, 5 cm from the anus were observed and recorded.

(VII) On day 8, the test drugs were administrated twice a day for 28 days according the group. The drugs daily administration time was 9:00-11:00 and 16:30-18:30.

(VIII) Blood samples were collected by heparin lithium anticoagulant tube on day 0 (before induced), day 7 (after induced), day 8 (the initial day of administrating of the test drug) and days 12, 14 and 35. The tubes were centrifuged at 3000 rpm and then analyzed.

(IX) On day 35, the inflamed tissue and normal tissue were taken by endoscopic biopsy (about 5-10 cm from the anus).

Result:

The result of the recovery rate of different groups by the period of time was shown in Table 3. From Table 3, it can be known that the group A (HA plus 400 mg 5-ASA/day) has better recovery rate than group B (placebo) and group C (1000 mg 5-ASA/day). The result proves that the effect of HA plus drug can decrease the dose or amount of the drug used, which is consistent with the result of the embodiment 2 above, and thus the formulation of the pellet 100a has even better therapy effect than the single drug with regular dose.

TABLE 3

Recovery rate of different groups by the period of time

| *Recovery rate | Group A | Group B | Group C |
|---|---|---|---|
| D7-D14 | 45 ± 16 | 22 ± 20 | 41 ± 19 |
| D7-D35 | 81 ± 5 | 50 ± 0 | 62 ± 7 |
| D7-D49 | 88 ± 3 | 73 ± 20 | 66 ± 5 |

*The value of the recovery rate is written as mean ± SD.

The concentration of 5-ASA (i.e. mesalamine) and N-Acetyl-5-ASA (a metabolite of 5-ASA) in the plasma of different groups was shown in Table 4. The lower the 5-ASA concentration in the plasma was, the smaller the side effect. In Table 4, the average concentration of 5-ASA in the plasma of group A was less than that of group C, which means the dosage form of HA plus drug eliminate the safety issue.

TABLE 4

| *Plasma Conc. (ng/mL) | Group A | | Group B | | Group C | |
|---|---|---|---|---|---|---|
| | 5-ASA | N-Acetyl-5-ASA | 5-ASA | N-Acetyl-5-ASA | 5-ASA | N-Acetyl-5-ASA |
| D0 | 0 | 0 | 0 | 0 | 0 | 0 |
| D7 | 0 | 0 | 0 | 0 | 0 | 0 |
| D8 | 14.9 | 253.5 ± 41.7 | 0 | 0 | 32.8 ± 8.1 | 802.3 ± 141.8 |
| D12 | 30.0 ± 5.4 | 745.9 ± 301.7 | 0 | 0 | 398.5 ± 351.1 | 4119.8 ± 2116.5 |
| D14 | 144.5 ± 76.8 | 1448.3 ± 644.1 | 0 | 0 | 389.6 ± 204.5 | 3595.1 ± 1555.9 |
| D35 | 109.5 ± 63.6 | 1927.8 ± 367.9 | 0 | 0 | 303.0 ± 224.2 | 3567.1 ± 1300.8 |

*The plasma concentration is written as mean ± SD.

Although the present invention has been described in considerable detail with reference to certain embodiments thereof, other embodiments are possible. Therefore the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A pharmaceutical formulation containing at least a pellet,
    the pellet comprising:
    a core comprising a pharmaceutically acceptable inert material;
    a drug layer surrounding the core, wherein the drug layer comprises a therapeutically effective amount of a drug for treating an enteric disease;
    a glycosaminoglycan layer directly surrounding the drug layer, wherein the glycosaminoglycan layer comprises a glycosaminoglycan;
    an isolation layer surrounding the glycosaminoglycan layer, wherein the isolation layer comprises a hydrophobic polymer, which is dissolved at a pH value of at least 5.5; and
    an enteric coating layer surrounding the isolation layer, wherein the enteric coating layer comprises an enteric polymer, which is dissolved at a pH value of at least 6.8.

2. The pharmaceutical formulation of claim 1, wherein the weight ratio of the core, the drug layer, the glycosaminoglycan layer, the isolation layer, and the enteric coating is 100:137-141:25-29:9-13:60-64.

3. The pharmaceutical formulation of claim 1, wherein the pharmaceutically acceptable inert material is cellulose, starch, sugar, or silicon oxide.

4. The pharmaceutical formulation of claim 1, wherein the drug layer further comprises a binder.

5. The pharmaceutical formulation of claim 4, wherein the binder is hydroxypropylmethyl cellulose, hydroxypropyl cellulose, or polyvinylpyrrolidone.

6. The pharmaceutical formulation of claim 1, wherein the drug is selected from the group consisting of mesalamine, laxatives, anti-diarrheals, glucocorticoids, antimicrobials, immunosuppressants, chemotherapeutics, anti-cancer drugs, peptides, proteins, cardiovascular drugs, psychotropic drugs, H2-blockers, antiasthmatic agents, antihistamines, steroid, non-steroid anti-inflammatory drug (NSAID), antibiotic, anti-inflammatory, and any derivatives thereof.

7. The pharmaceutical formulation of claim 1, wherein the glycosaminoglycan is hyaluronic acid or a salt thereof, chondroitin sulfates, heparin sulfate, heparin, keratan sulfate, or dermatan sulfate.

8. The pharmaceutical formulation of claim 1, wherein the hydrophobic polymer is poly (methacrylic acid-co-ethyl acrylate) 1:1, poly (methacylic acid-co-methyl methacrylate) 1:1, poly (methyl acrylate-co-methyl methacrylate-co-methacrylic acid) 7:3:1, cellulose acetate phthalate, cellulose acetate succinate, methylcellulose phthalate, methylhydroxypropyl-cellulose phthalate, ethylhydroxycellulose phthalate, polyvinylacetate phthalate, polyvinylbutyrate acetate, vinyl acetate-maleic anhydride copolymer, styrene-maleic mono-ester copolymer, methyl acrylate-methacrylic acid copolymer, or methacrylate-methacrylic acid-octyl acrylate copolymer.

9. The pharmaceutical formulation of claim 1, wherein the enteric polymer is selected from the group consisting of cellulose acetate phthalate, cellulose acetate succinate, methylcellulose phthalate, methylhydroxypropyl-cellulose phthalate, ethylhydroxycellulose phthalate, polyvinylacetate phthalate, polyvinylbutyrate acetate, vinyl acetate-maleic anhydride copolymer, styrene-maleic mono-ester copolymer, methyl acrylate-methacrylic acid copolymer, and methacrylate-methacrylic acid-octyl acrylate copolymer.

10. The pharmaceutical formulation of claim 1, wherein the pellet is in a capsule or a tablet.

11. A pharmaceutical formulation containing at least a pellet, the pellet comprising:
    a core comprising a pharmaceutically acceptable inert material;
    a drug layer surrounding the core, wherein the drug layer comprises a therapeutically effective amount of a drug for treating an enteric disease, and the drug is selected from the group consisting of mesalamine, laxatives, anti-diarrheals, glucocorticoids, antimicrobials, immunosuppressants, chemotherapeutics, anti-cancer drugs, peptides, proteins, cardiovascular drugs, psychotropic drugs, H2-blockers, antiasthmatic agents, antihistamines, steroid, non-steroid anti-inflamatory drug (NSAID), antibiotic, anti-inflammatory, and any derivatives thereof;
    a glycosaminoglycan layer directly surrounding the drug layer, wherein the glycosaminoglycan layer comprises a glycosaminoglycan, and the glycosaminoglycan is hyaluronic acid or a salt thereof, chondroitin sulfates, heparin sulfate, heparin, keratan sulfate, or dermatan sulfate; and
    an enteric coating layer surrounding the glycosaminoglycan layer, wherein the enteric coating layer comprises an enteric polymer, which is dissolved at a pH value of at least 6.8.

12. The pharmaceutical formulation of claim 11, wherein the weight ratio of the core, the drug layer, the glycosaminoglycan layer, and the enteric coating is 100:137-141:25-29:60-64.

13. The pharmaceutical formulation of claim 11, wherein the pharmaceutically acceptable inert material is cellulose, starch, sugar, or silicon oxide.

14. The pharmaceutical formulation of claim 11, wherein the drug layer further comprises a binder.

15. The pharmaceutical formulation of claim 14, wherein the binder is hydroxypropylmethyl cellulose, hydroxypropyl cellulose, or polyvinylpyrrolidone.

16. The pharmaceutical formulation of claim 11, wherein the enteric polymer is selected from the group consisting of cellulose acetate phthalate, cellulose acetate succinate, methylcellulose phthalate, methylhydroxypropyl-cellulose phthalate, ethylhydroxycellulose phthalate, polyvinylacetate phthalate, polyvinylbutyrate acetate, vinyl acetate-maleic anhydride copolymer, styrene-maleic mono-ester copolymer, methyl acrylate-methacrylic acid copolymer, and methacrylate-methacrylic acid-octyl acrylate copolymer.

17. The pharmaceutical formulation of claim 11, wherein the pellet is in a capsule or a tablet.

* * * * *